United States Patent [19]
Kim et al.

[11] Patent Number: 6,156,909
[45] Date of Patent: Dec. 5, 2000

[54] PREPARATION OF ALKYLENE CARBONATE USING INDIUM HALIDES AND MIXTURES OF SAME WITH LEAD HALIDES AS CATALYST

[75] Inventors: Hoon Sik Kim, Seoul; Jai Jun Kim, Kyunggido; Sang Deuk Lee, Seoul; Kun You Park, Seoul; Hong Gon Kim, Seoul, all of Rep. of Korea

[73] Assignee: Korea Institute of Science & Technology, Seoul, Rep. of Korea

[21] Appl. No.: 09/477,829

[22] Filed: Jan. 5, 2000

[30] Foreign Application Priority Data

Jul. 26, 1999 [KR] Rep. of Korea ............... 99-30402

[51] Int. Cl.<sup>7</sup> ............... C07D 317/36; C07D 317/38
[52] U.S. Cl. ............... 549/230
[58] Field of Search ............... 549/230

[56] References Cited

U.S. PATENT DOCUMENTS 5,350,862   9/1994   Wagner et al. ............... 549/230

FOREIGN PATENT DOCUMENTS 45-38534   12/1970   Japan .

*Primary Examiner*—Bernard Dentz
*Attorney, Agent, or Firm*—Arent Fox Kintner Plotkin & Kahn, PLLC

[57] ABSTRACT

The present invention relates to a method for preparing alkylene carbonate by reacting alkylene oxide with carbon dioxide in the presence of a catalyst system comprising:

a) at least one selected from the group consisting of $PbY_2$, $InY_3$ and their mixture, wherein Y is Cl, Br or I; and b) at least one alkali metal halide selected from the group consisting of MCl, MBr and MI, wherein M is alkali metal.

14 Claims, No Drawings

PREPARATION OF ALKYLENE CARBONATE USING INDIUM HALIDES AND MIXTURES OF SAME WITH LEAD HALIDES AS CATALYST

BACKGROUND OF THE INVENTION

1. Field of the Invention

The present invention relates to a method for preparing alkylene carbonate by reacting alkylene oxide with carbon dioxide. More particularly, the present invention relates to a method for preparing alkylene carbonate by reacting alkylene oxide with carbon dioxide in the presence of a catalyst system comprising a) $PbY_2$, $InY_3$ or their mixture and b) MX (M: alkali metal, X, Y: halide).

2. Description of the Prior Art

Alkylene carbonates are used in polycarbonate synthesis, as an intermediate in pharmaceutical processes, an oxyalkylation agent in dyestuff syntheses and a solvent in textile production processes. Conventionally, alkylene carbonate has been produced by reacting alkylene oxide with carbon dioxide in the presence of a catalyst, as shown in scheme 1.

Scheme 1

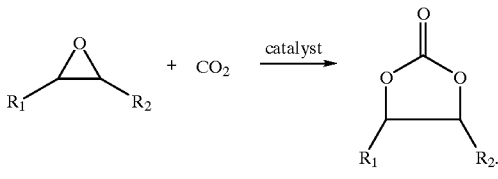

There are substantial literatures in the art with respect to the catalytic reaction of the alkylene oxide and carbon dioxide. Numerous catalysts have been proposed including alkali or alkali earth metal halide, ammonium halide and phosphonium halides.

For example, U.S. Pat. No. 4,881,555, U.S. Pat. No. 4,931,571 and Japanese Laid-Open Patent No. 7-206846 teaches a process for preparing an alkylene carbonate that employs a catalyst selected from the group consisting of organic quaternary ammonium halide, organic quaternary phosphonium halide, organic sulfonium halides and organic antimony halides. Japanese Laid-Open Patent No. 9-067365 discloses a method for preparing an alkylene carbonate, wherein a catalyst comprising an alkali or alkali earth metal halide is used. Japanese Laid-Open Patent No. 8-059557 also discloses an alkali halide catalyst.

U.S. Pat. No. 2,773,070 introduces as a catalyst an ion exchange resin containing quaternary phosphonium halide groups, and U.S. Pat. No. 4,233,221 discloses DOWEX and Amberlite ion exchange resin. It was found that the anion-exchange resin catalysts lose their catalytic activity over a period of use.

U.S. Pat. No. 4,665,467 and U.S. Pat. No. 5,283,356 disclose methods for preparing alkylene carbonate by using a phthalocyanine or a porphyrine catalyst containing Co, Cr, Fe, Mn, Ni, Ti, V and Zr. In addition, JP 7-206847 discloses a process for preparing alkylene carbonate by using a rubidium or cesium substituted heteropoly acid catalyst.

In order to provide an attractive process for preparing alkylene carbonate, the process should achieve high selectivity to alkylene carbonate and should be economical. However, the processes disclosed in the above literatures has one or more problems in terms of yield, reaction condition, cost, etc.

SUMMARY OF THE INVENTION

An object of the present invention is to provide a method of producing alkylene carbonate with a high yield, in a short reaction time and under mild reaction conditions. More particularly, the object of the present invention is to provide a method of producing alkylene carbonate under milder reaction condition by using a new catalyst system comprising a) lead halides, indium halides or their mixture and b) alkali metal halides.

DETAILED DESCRIPTION OF THE INVENTION

The present invention is directed to a new method of preparing alkylene carbonate by reacting alkylene oxide with carbon-dioxide, which obviates above mentioned prior art's problem.

The present invention provides a new method of preparing alkylene carbonate by reacting alkylene oxide with carbon dioxide in the presence of a catalyst system comprising a) lead halides, indium halides, or their mixture and b) alkali metal halides.

The present inventors have found that a catalyst system comprising a) lead halide, indium halides or their mixture and b) alkali metal halides is more effective than the conventional catalyst system in preparing alkylene carbonate of the formula

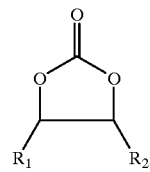

wherein $R_1$ and $R_2$ are independently hydrogen or $C_1 \sim C_4$ alkyl group.

Lead halides ($PbY_2$) used in the present invention include $PbCl_2$, $PbBr_2$ and $PbI_2$, indium halides ($InY_3$) include $InCl_3$, $InBr_3$ and $InI_3$, and the alkali metal halides (MX) include NaCl, NaBr, NaI, KCl, KBr, KI, RbCl, RbBr, RbI, CsCl, CsBr and CsI. Preferable alkali metal is Na or K.

It is preferable to include at least one Br or I in lead halides, indium halides and alkali metal halides. In composing a catalyst system expressed as $a[PbY_2]/b[MX]$ and/or $a[in\ Y_3]/b[MX]$, the ratio between a and b is preferably a:b=1:20~5:1, more preferably 1:2~1:3.

The amount of catalyst is preferably 0.005–3 mol % of the alkylene oxide.

Since the reaction is not greatly influenced by nitrogen, hydrogen, hydrocarbons and water typically present in carbon dioxide and alkylene oxide, it is possible to use commercially available carbon dioxide and alkylene oxide without a purification step.

Considering the equipment and operating cost, it is preferable to operate a reaction at a pressure of 10~100 atm, and a temperature of 80~180° C.

Although the above reaction can be performed in the absence of a solvent, it is possible to use a solvent to prevent excessive heat production during the reaction. As a solvent, alkylene carbonate identical with the one to be produced from the reaction is preferable. Thus, ethylene carbonate is a preferable solvent when ethylene carbonate is synthesized from ethylene oxide, and propylene carbonate is preferable when propylene carbonate is synthesized from propylene oxide. Alkylene carbonate different from the one to be produced from the reaction can be also used as a solvent. For example, propylene carbonate can be used as a solvent in the synthesis of ethylene carbonate (see Examples 56–59).

The reaction could be performed by a batch process using the reactor provided with a stirrer or by a continuous process using a bubble column.

EXAMPLES

The present invention will be further illustrated by the following examples, but, of course, should not construed as in any way limiting its scope.

Example 1

After ethylene oxide (16.80 g, 380 mmol), KI (284 mg, 1.71 mmol) and $InCl_3$ (183 mg, 0.83 mmol) were added to a 200 ml high pressure reactor, the reactor was pressurized to 10 atm with $CO_2$. The reactor was heated to 100° C., and then carbon dioxide was injected again to the pressure of 30 atm. During the reaction, carbon dioxide was continuously supplied to maintain the pressure of the reactor at 30 atm. After the reaction at 100° C. for 1 hour, the reactor was cooled to room temperature. Volatiles were removed and the solid product was isolated and weighed to be 33.2 g. The yield analyzed by gas-liquid chromatography was 99%.

The yield was calculated as follows:

$$\text{Yield of alkylene carbonate (\%)} = \frac{\text{Moles of produced alkylene carbonate}}{\text{Moles of reactant alkylene oxide}} \times 100$$

Examples 2~15

The process of Example 1 was repeated except that different catalyst systems comprising $PbX_2$ and alkali metal halide were employed in place of catalyst system comprising $InI_3$ and KI. The results are shown in Table 1.

TABLE 1

| Example | Catalyst system | | Product weight (g) | Yield (%) |
|---|---|---|---|---|
| 2 | $PbCl_2$ | NaBr | 5.0 | 15 |
| 3 | | NaI | 31.6 | 94 |
| 4 | $PbBr_2$ | NaBr | 7.1 | 21 |
| 5 | | NaI | 32.6 | 97 |
| 6 | $PbI_2$ | NaCl | 19.5 | 58 |
| 7 | | NaBr | 23.8 | 71 |
| 8 | | NaI | 33.2 | 99 |
| 9 | $PbCl_2$ | KBr | 4.0 | 12 |
| 10 | | KI | 32.9 | 98 |
| 11 | $PbBr_2$ | KBr | 10.1 | 30 |
| 12 | | KI | 32.9 | 98 |
| 13 | $PbI_2$ | KCl | 22.8 | 68 |
| 14 | | KBr | 26.2 | 78 |
| 15 | | KI | 33.2 | 99 |

Examples 16~28

The process of Example 1 was repeated except that different catalyst systems comprising indium halide and alkali metal halide were employed in place of catalyst system comprising $InI_3$ and KI. The results are shown in Table 2.

TABLE 2

| Example | Catalyst system | | Product weight (g) | Yield (%) |
|---|---|---|---|---|
| 16 | $InCl_3$ | NaBr | 4.0 | 12 |
| 17 | | NaI | 32.9 | 98 |
| 18 | $InBr_3$ | NaBr | 9.4 | 28 |
| 19 | | NaI | 33.2 | 96 |
| 20 | $InI_3$ | NaCl | 27.9 | 83 |
| 21 | | NaBr | 29.9 | 89 |
| 22 | | NaI | 33.2 | 99 |
| 23 | $InCl_3$ | KBr | 5.7 | 17 |
| 24 | $InBr_3$ | KBr | 12.8 | 38 |
| 25 | | KI | 32.9 | 98 |
| 26 | $InI_3$ | KCl | 31.9 | 95 |
| 27 | | KBr | 32.6 | 97 |
| 28 | | KI | 33.2 | 99 |

Examples 29~39

The process of Example 1 was repeated except that different catalyst systems comprising lead or indium halide and alkali metal halide were employed and the molar ratios of lead or indium halide to alkali metal halide were in the range of 1:20~5:1. The results are shown in Table 3.

TABLE 3

| Example | Catalyst system | a:b | Product weight (g) | Yield (%) |
|---|---|---|---|---|
| 29 | $PbBr_2$:KI | 1:5 | 27.9 | 83 |
| 30 | $PbBr_2$:KI | 1:1 | 32.2 | 96 |
| 31 | $PbBr_2$:KI | 3:1 | 26.2 | 78 |
| 32 | $PbI_2$:KBr | 1:10 | 7.7 | 23 |
| 33 | $PbI_2$:KBr | 1:1 | 23.8 | 71 |
| 34 | $PbI_2$:KBr | 2:1 | 26.9 | 80 |
| 35 | $PbI_2$:KBr | 5:1 | 27.5 | 82 |
| 36 | $InCl_3$:NaI | 1:20 | 5.4 | 16 |
| 37 | $InCl_3$:NaI | 1:10 | 17.8 | 53 |
| 38 | $InCl_3$:NaI | 1:5 | 30.6 | 91 |
| 39 | $InCl_3$:NaI | 1:1 | 32.9 | 98 |

Examples 40~43

The process of Example 1 was repeated except that the reaction temperatures were in the range of 80~180° C. The results are shown in Table 4.

TABLE 4

| Example | Reaction Temperature (° C.) | Product weight (g) | Yield (%) |
|---|---|---|---|
| 40 | 80 | 29.2 | 87 |
| 41 | 120 | 33.2 | 99 |
| 42 | 150 | 32.6 | 97 |
| 43 | 180 | 31.2 | 93 |

Examples 44~47

The process of Example 1 was repeated except that the reaction pressures the range of 10~100 atm. The results are shown in Table 5.

TABLE 5

| Example | Reaction Pressure (atm) | Product weight (g) | Yield (%) |
|---|---|---|---|
| 44 | 10 | 22.8 | 68 |
| 45 | 50 | 33.3 | 99 |
| 46 | 70 | 33.2 | 99 |
| 47 | 100 | 33.2 | 99 |

Examples 48~52

The process of Example 1 was repeated except that the molar ratios of a catalyst mixture to the ethylene oxide were in the range of 0.005~3. The results are shown in Table 6.

TABLE 6

| Example | Catalyst mixture/ ethylene oxide (mol %) | Product weight (g) | Yield (%) |
| --- | --- | --- | --- |
| 48 | 0.005 | 5.7 | 17 |
| 49 | 0.1 | 17.1 | 51 |
| 50 | 0.5 | 33.2 | 99 |
| 51 | 1 | 33.2 | 99 |
| 52 | 3 | 33.2 | 99 |

Examples 53~55

The process of Example 1 was repeated except that the different alkylene oxides were employed. The results are shown in Table 7.

TABLE 7

| Example | Reactant/Product | Product weight (g) | Yield (%) |
| --- | --- | --- | --- |
| 53 | Propylene oxide/ Propylene carbonate | 32.2 | 96 |
| 54 | 2-methyl-1,2-epoxypropane/ 1,2-dimethylene carbonate | 27.5 | 82 |
| 55 | 2,3-epoxy butane/ 1,2-dimethylethylene carbonate | 23.8 | 71 |

Examples 56~59

The process of Example 1 was repeated except that the different solvents and/or the different amounts thereof were employed. The results are shown in Table 8.

TABLE 8

| Example | Solvent | Solvent/ ethylene oxide (wt %) | Product weight (g) | Yield (%) |
| --- | --- | --- | --- | --- |
| 56 | Ethylene carbonate | 50 | 32.9 | 98 |
| 57 | Propylene carbonate | 100 | 32.2 | 96 |
| 58 | Ethylene carbonate | 150 | 30.6 | 91 |
| 59 | Propylene carbonate | 200 | 27.9 | 83 |

Examples 60~62

The process of Example 1 was repeated except that different catalyst systems comprising lead halide, indium halide and alkali metal halide were employed in place of catalyst system comprising $InI_3$ and KI. The results are shown in Table 9.

TABLE 9

| Example | Catalyst | Catalyst ratio | Product weight (g) | Yield (%) |
| --- | --- | --- | --- | --- |
| 60 | $PbCl_2$/NaI/KBr | 2:1:1 | 33.2 | 99 |
| 61 | $PbCl_2$/$InI_3$/KBr | 1:1:2 | 32.2 | 96 |
| 62 | $PbCl_2$/$InI_3$/NaCl | 1:1:2 | 33.2 | 99 |

According to the present invention, alkylene carbonate can be economically produced from alkylene oxide and carbon dioxide by using the catalyst system comprising a) lead halides, indium halides or their mixture and b) alkali metal halides.

What is claimed is:

1. A method for preparing alkylene carbonate by reacting alkylene oxide with carbon dioxide in the presence of a catalyst, characterized in that the catalyst comprises:

a) at least one indium halide selected from the group consisting of $InCl_3$, $InBr_3$ and $InI_3$ and their mixture or a mixture of at least one of the preceding with at least one lead halide selected from the group consisting of $PbCl_2$, $PbBr_2$ and $PbI_2$; and b) at least one alkali metal halide selected from the group consisting of MCl, MBr and MI, wherein M is alkali metal.

2. A method according to claim 1, wherein the catalyst comprises:

a) at least one indium halide selected from the group consisting of $InCl_3$, $InBr_3$ and $InI_3$; and 3.b) at least one alkali metal halide selected from the group consisting of MCl, MBr and MI wherein M is alkali metal.

3. A method according to claim 1, wherein the catalyst comprises:

a) at least one lead halide selected from the group consisting of $PbCl_2$, $PbBr_2$ and $PbI_2$;

b) at least one indium halide selected from the group consisting of $InCl_3$, $InBr_3$ and $InI_3$; and c) at least one alkali metal halide selected from-the group of MCl, MBr and MI, wherein M is alkali metal.

4. A method according to claim 1, wherein the alkali metal is Na or K.

5. A method according to claim 1, wherein said at least one indium halide is selected from $InCl_3$ and $InBr_3$.

6. A method according to claim 1, wherein the molar ratio of a)/b) is in the range of 1:20~5:1.

7. A method according to claim 1, wherein the amount of catalysts is in the range of 0.005~3 mol % based on the raw material alkylene oxide.

8. A method according to claim 1, wherein the reaction temperature is in the range of 80~180° C.

9. A method according to claim 1, wherein the reaction pressure is in the range of 10~100 atm.

10. A method according to claim 1, wherein the reaction is carried out without a solvent.

11. A method according to claim 1, wherein the reaction is carried out with a solvent.

12. A method according to claim 11, wherein the solvent is the same with the produced alkylene carbonate.

13. A method according to claim 11, wherein the solvent is ethylene carbonate or propylene carbonate.

14. A method according to claim 1, wherein the alkylene carbonate produced has the following formula:

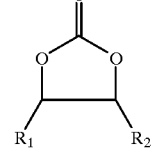

wherein $R_1$ and $R_2$ are independently hydrogen or $C_1$~$C_4$ alkyl group.

* * * * *